United States Patent [19]

Shubert et al.

[11] Patent Number: 4,864,027

[45] Date of Patent: Sep. 5, 1989

[54] SILANE DERIVATIVES

[75] Inventors: Hans H. Shubert, Frankfurt am Main; Gerhard Salbeck, Hofheim am Taunus; Walter Lüders, Heusenstamm; Werner Knauf, Eppstein, all of Fed. Rep. of Germany

[73] Assignee: Hoechst Aktiengesellschaft, Frankfurt am Main, Fed. Rep. of Germany

[21] Appl. No.: 211,155

[22] Filed: Jun. 22, 1988

Related U.S. Application Data

[63] Continuation of Ser. No. 922,734, Oct. 24, 1986, abandoned.

[30] Foreign Application Priority Data

Oct. 26, 1985 [DE] Fed. Rep. of Germany ....... 3538139
May 31, 1986 [DE] Fed. Rep. of Germany ....... 3618354

[51] Int. Cl.$^4$ .................... C07F 7/10; A61K 31/695
[52] U.S. Cl. .................... 546/14; 556/406; 556/444; 556/445; 556/448; 556/465; 548/406; 549/4; 549/214; 568/639; 568/635; 546/216
[58] Field of Search .............. 556/406, 444, 445, 448, 556/465; 548/406; 549/4, 214; 546/14, 63

[56] References Cited

U.S. PATENT DOCUMENTS 3,334,123 8/1967 Culpepper ........................... 556/448
3,362,933 1/1968 Culpepper ........................... 556/448

FOREIGN PATENT DOCUMENTS 0068813 9/1985 European Pat. Off. ............ 548/110

OTHER PUBLICATIONS

Japanese published specification No. 60/123,491 plus English translation.

*Primary Examiner*—Robert T. Bond
*Attorney, Agent, or Firm*—Curtis, Morris & Safford

[57] ABSTRACT

The compounds of the formula (I)

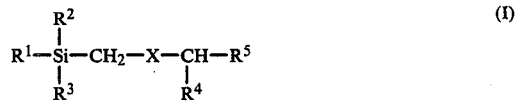

in which
 X denotes $CH_2$, O, S or $NR^6$,
 $R^1$ denotes alkyl, cycloalkyl, alkenyl, (substituted) phenyl, or (substituted) naphthyl,
 $R^2$ and $R^3$ denote alkyl, alkenyl or phenyl, or $R^2$ and $R^3$ together denote an alkylene chain,
 $R^4$ denotes —H, —CN, —$CCl_3$, —C≡CH, alkyl, F, or —C(S)—$NH_2$,
 $R^5$ denotes pyridyl, furyl, thienyl, phthalimidyl, di($C_1$-$C_4$)alkylmaleinimidyl, thiophthalimidyl, dihydrophthalimidyl or tetrahydrophthalimidyl, which may all be substituted, or substituted phenyl, or
 $R^4$ and $R^5$—together with the carbon atom bridging them—denote an optionally substituted indanyl, cyclopentenoyl or cyclopentenyl radical, with the proviso that compounds of the formula I in which
 $R^1$ denotes phenyl which is substituted in the para-position by ($C_1$-$C_4$)alkoxy, halogen or ($C_1$-$C_4$)alkyl;
 $R^2$ and $R^3$ denote $CH_3$;
 X denotes O;
 $R^4$ denotes H and
 $R^5$ denotes 3-phenoxyphenyl or (4-fluoro-3-phenoxy)phenyl being excepted, have advantageous insecticidal, acaricidal and nematocidal properties.

5 Claims, No Drawings

SILANE DERIVATIVES

This application is a continuation of application Ser. No. 922,734, filed Oct. 24, 1986.

The basic structures known hitherto of insecticidal, acaricidal and nematocidal active compounds include such differing groups of substances as, for example, the phosphoric acid derivatives, the chlorohydrocarbons, the N-methylcarbamates, the cyclopropanecarboxylates and the benzoylureas, to mention just a few of the most important. Amazingly, however, (with a single exception, see Japanese Published Specification No. 60/123,491) no insecticidal, acaricidal and nematocidal compounds which contain a basic structure containing the element silicon have hitherto been described (C. Worthing, The Pesticide Manual, 7th edition, Lavenham 1983; S. Pawlenko, Organo-SiliciumVerbindungen [Organosilicon Compounds] in: Methoden der org. Chemie [Methods of Organic Chemistry] (Houben-Weyl), Volume XIII/5, Georg Thieme Verlag, Stuttgart 1980; R. Wegler, Chemie der Pflanzenschultz- und Schädlingsbekämpfungsmittel [The Chemistry of Plant-Protection Agents and Pesticides], Vols. 1, 6 and 7, Springer-Verlag, Berlin 1970, 1981). The same fact applies to the herbicide sector, and fungicide research has also only led to one case hitherto of the discovery of a silicon-containing basic structure for triazol fungicides (EP-A 68,813).

Novel active compounds having a silicon-containing basic structure have now been found which have advantageous applicational properties in the area of the insecticides, acaricides and nematocides.

The present invention thus relates to the compounds of the formula (I), the various optical isomers, and their possible mixtures,

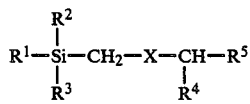
(I)

wherein

X denotes $CH_2$, O, S or $NR^6$, $R^1$ denotes $(C_2-C_{18})$alkyl, $(C_5-C_7)$cycloalkyl, $(C_2-C_8)$-alkenyl, phenyl or naphthyl, all these substituents being optionally mono- or polysubstituted, with the exception of pentafluorophenyl, $R^2$ and $R^3$, independently of one another, denote $(C_1-C_3)$alkyl, $(C_2-C_8)$alkenyl, or phenyl, or $R^2$ and $R^3$ together denote an alkylene chain which—together with the silicon atom—produces an unsubstituted or $(C_1-C_4)$alkylsubstituted heterocycle having 4 to 6 ring members, $R^4$ denotes —H, —CN, —$CCl_3$, —C≡CH, $(C_1-C_4)$alkyl, F or

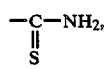

$R^5$ denotes pyridyl, furyl or thienyl, which can all be substituted, phthalimidyl, di($C_1-C_4$)alkylmaleinimidyl, thiophthalimidyl, dihydrophthalimidyl, tetrahydrophthalimidyl, or substituted phenyl with the exception of 4-acetylphenyl, 2-chlorophenyl and 4-ethoxycarbonylacetylphenyl or $R^4$ and $R^5$—together with the carbon atom bridging them—denote an optionally substituted indanyl, cyclopentenoyl or cyclopentenyl radical, and $R^6$ denotes H, ($C_1-C_3$)alkyl or phenyl, with the proviso that the compounds of the formula (I) in which $R^1$ denotes phenyl which is substituted in the paraposition by ($C_1-C_4$)alkoxy, halogen or ($C_1-C_4$)alkyl;

$R^2$ and $R^3$ denotes $CH_3$; X denotes O; $R^4$ denotes H, and $R^5$ denotes 3-phenoxyphenyl or (4-fluoro-3-phenoxy)phenyl are excluded.

Optionally substituted alkyl for $R^1$ preferably represents ($C_2-C_{12}$)alkyl which may be substituted by halogen or ($C_1-C_4$)alkoxy. Examples which may be mentioned as optionally substituted ethyl, n-propyl, i-propyl, n-butyl, t-butyl, 3,3-dimethylbutyl, n-octyl, n-decyl, n-dodecyl and n-octadodecyl.

Optionally substituted cycloalkyl for $R^1$ preferably represents optionally mono- or disubstituted cyclohexyl, preferred substituents being $C_1-C_4$)alkyl, halogen and $C_1-C_4$)alkoxy.

Optionally substituted alkenyl for $R^1$ preferably represents ($C_4-C_8$)alkenyl which can be mono- or polysubstituted by halogen and/or mono- or disubstituted by ($C_1-C_4$)alkoxy. Examples which may be mentioned are optionally substituted 3-butenyl, 5-hexenyl and 7-octenyl.

Optionally substituted phenyl or naphthyl for $R^1$ preferably represent a phenyl or naphthyl radical of the general formula (A) or (B),

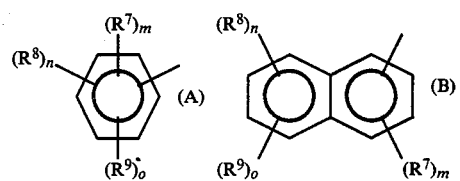

in which $0 \leq m+n+o \leq 4$ and m, n and o can have the values 0 to 4 in the case of formula (A) or 0 to 3 in the case of formula (B).

$R^7$, $R^8$ and $R^9$, independently of one another, represent optionally hydroxy-substituted ($C_1-C_4$)-alkyl, tri($C_1-C_4$)alkylsilyl, halogen, nitro, cyano, ($C_2-C_6$)alkenyl, ($C_2-C_6$)-alkinyl, amino, ($C_3-C_7$)cycloalkyl, phenyl, phenoxy, ($C_1-C_5$)alkoxy, ($C_2-C_4$)alkenyloxy, ($C_2-C_4$)alkinyloxy, hydroxycarbonyl, ($C_1-C_4$)alkylthio, ($C_3-C_7$)cycloalkyloxy, ($C_1-C_6$)alkylcarbonyl, ($C_1-C_4$)alkoxycarbonyl, ($C_2-C_4$)alkenyloxycarbonyl, ($C_3-C_5$)alkinyloxycarbonyl, ($C_1-C_4$)haloalkyl, ($C_1-C_4$)alkoxy($C_1-C_4$)alkyl, ($C_1-C_3$)haloalkoxy, ($C_1-C_3$)-haloalkylthio, halo($C_1-C_4$)alkoxy($C_1-C_4$) alkyl, ($C_1-C_4$)alkylthio($C_1-C_4$)alkyl, ($C_1-C_4$)alkoxy($C_1-C_4$)alkoxy, halo($C_1-C_4$)alkoxy($C_1-C_4$)alkoxy, ($C_2-C_4$)-alkenyloxy($C_1-C_4$)alkoxy, halo($C_2-C_4$)alkenyloxy, ($C_1-C_4$)alkoxy($C_1-C_4$)alkylthio, ($C_1-C_4$)alkylthio($C_1-C_4$)alkoxy, ($C_1-C_4$)alkylthio($C_1-C_4$)alkylthio, halo($C_1-C_4$)alkoxycarbonyl, halo($C_2-C_4$)alkenyloxycarbonyl or di($C_1-C_6$alkyl)amino, or two of the radicals $R^7$, $R^8$ and $R^9$, if they are in the ortho-positions to one another, form a methylenedioxy, ethylenedioxy or ($C_3-C_5$)alkylene radical.

$R^7$, $R^8$ and $R^9$ preferably denote halogen, ($C_1-C_4$)alkyl, ($C_2-C_6$)alkenyl, ($C_3-C_7$)cycloalkyl, ($C_1-C_5$)-alkoxy, ($C_2-C_4$)alkenyloxy, ($C_1-C_4$)haloalkyl or ($C_1-C_3$)haloalkoxy.

The radical $R^1$ preferably denotes the phenyl radical which has 0–3 substituents from the selection specified for $R^7$–$R^9$. Particularly preferred phenyl radicals are those having 1–3, particularly having 1–2, substituents in the m- or p-position, selected from the radicals $R^7$–$R^9$ described above, halogen, $(C_1$–$C_4)$alkyl, $(C_1$–$C_4)$haloalkyl, $(C_1$–$C_3)$haloalkoxy and $(C_1$–$C_5)$-alkoxy being preferred.

Specific examples of the radical $R^1$ are listed below, although the radicals $R^1$ coming within the scope of the invention are not limited to those which are mentioned as examples.

The following are mentioned as specific examples of $R^1$: ethyl, n-propyl, i-propyl, n-butyl, 3,3-dimethylbutyl, n-octyl, n-decyl, n-octadecyl, cyclohexyl, benzyl, 5-hexenyl, 7-octenyl, 1-naphthyl, phenyl, 3-methylphenyl, 4-methylphenyl, 3,4-dimethylphenyl, 4-chlorophenyl, 3-trifluoromethylphenyl, 4-trifluoromethylphenyl, 2-naphthyl, 3,4-dichlorophenyl, 4-nitrophenyl, 4-methylthiophenyl, 4-methoxyphenyl, 3,4-dimethoxyphenyl, 3,4-methylenedioxyphenyl, 4-difluoromethylthiophenyl, 4-trifluoromethylthiophenyl, 3,4-difluoromethylenedioxyphenyl, 4-cyanophenyl, 4-fluorophenyl, 4-bromophenyl, 3,4-difluorophenyl, 4-dibromophenyl, 4-chloro-3-fluorophenyl, 3-chloro-4-fluorophenyl, 3-chloro-4-methylphenyl, 3-bromo-4-chlorophenyl, 4-difluoromethoxyphenyl, 3,4-bis(difluoromethoxy)phenyl, 4-trifluoromethoxyphenyl, 3,4-bis(trifluoromethoxy)phenyl, 4-methoxy-3,5-dimethylphenyl, 3,4-trifluoroethylenedioxyphenyl, 4-tert.-butylphenyl, 4-ethylphenyl, 4-isopropylphenyl, 3,4-difluoroethylenedioxyphenyl, 4-isopropenylphenyl, 4-vinylphenyl, 4-(2,2-dichlorovinyl)phenyl, 4-chloro-3-methylphenyl, 3-bromo-4-fluorophenyl, 3-fluoro-4-bromophenyl, 4-fluoro-3-methylphenyl, 3-fluoro-4-methylphenyl, 3-bromo-4-methylphenyl, 3,4-diethylphenyl, 3,4-diisopropylphenyl, 3-ethyl-4-methylphenyl, 4-isopropyl-3-methylphenyl, 4-methylsulfoxyphenyl, 4-allylphenyl, 4-acetylphenyl, 4-carbethoxyphenyl, 4-ethoxyphenyl, 1,2,3,4-tetrahydronaphthalene-7-yl, 3,5-dichloro-4-methylphenyl, indane-5-yl, 4-propargylphenyl, 3-methoxy-4-methylphenyl, 4-methoxymethylphenyl, 4-(1-chloroethylene-1yl)phenyl, 4-(2-chloroallyl)phenyl, 4-isobutyrylphenyl, 4-methoxycarbonylphenyl, 3-nitro-4,5-dimethylphenyl, 3-ethoxy-4-bromophenyl, 3-chloro-4-methoxyphenyl, 4-bromo-3-chlorophenyl, 3,4-(di-tert.-butyl)phenyl, 4-ethyl-3-methylphenyl, 4-tert.-butyl-3-methylphenyl, 4-(1,1,2,2-tetrafluoroethoxy)phenyl, 4-(2,2-dichlorovinyloxy)phenyl, 4-(2,2,2-trifluoroethoxy)phenyl, 4-pentafluoroethoxyphenyl, 4-(chlorodifluoromethoxy)phenyl, 4-(chlorofluoromethoxy)phenyl, 4-(dichlorofluoromethoxy)phenyl, 4-(1,1-difluoroethoxy)phenyl, 4-(1,2,2-trichloro-1,2-difluoroethoxy)phenyl, 4-(2-bromo-1,1,2,2-tetrafluoroethoxy)phenyl, 4-(2-propynyloxy)phenyl, 4-(1-propynyloxy)phenyl, 4-allyloxyphenyl, 4-ethinyloxyphenyl, 4-(2-chloroethinyl)phenyl, 4-(n-propoxy)phenyl, 4-isopropoxyphenyl, 4-cyclopentyloxyphenyl, 4-(n-amyloxy)phenyl, 4-isobutoxyphenyl, 4-iodophenyl, 4-vinyloxyphenyl, 4-biphenyl, 4-(n-butoxy)phenyl, 4-(sec.-butoxy)phenyl, 6-methyl-2-naphthyl, 4-phenoxyphenyl, 4-(2-iodo-1,1-difluoroethoxy)phenyl, 4-cyclohexyloxyphenyl, 3-chloro-4-ethoxyphenyl, 4-formylphenyl, 4-ethoxymethylphenyl, 4-trifluoroacetyloxyphenyl, 4-(1-methoxyethyl)phenyl, 4-(1-ethoxyethyl)phenyl, 4-ethoxy-3-methylphenyl, 4-(2-methylpropenyl)phenyl, 4-(1,2,2-trifluorovinyloxy)phenyl, 3,4-diethoxyphenyl, 4-ethinylphenyl, 4-ethoxy-3,5-dimethylphenyl, 4-ethoxy-3-methoxyphenyl, 4-ethylthiophenyl, 4-(2,2,2-trifluoroethoxycarbonyl)phenyl, 4(2-chloroethoxy)phenyl, 4-(1-buten-2-yl)phenyl, 4-(2-buten-2-yl)phenyl, 4-methoxymethylthiophenyl, 4-(1,2-dichlorovinyloxy)phenyl, 4-(2,3-dichloroallyloxy)phenyl, 4-(2-iodo-1-fluorovinyloxy)phenyl, 4-(2-(fluoroethoxy)phenyl, 4-(2-chloro-1,1-difluoroethoxy)phenyl, 4-(2-chloro-1-fluorovinyloxy)phenyl, 4-isopropylthiophenyl, 4-(2,2-dichloro-1,1-difluoroethoxy)phenyl, 4-(2,2-dichloro-1-fluorovinyloxy)phenyl, 4-(1,1,2,2-tetrafluoroethoxy)phenyl, 3-chloro-4-ethoxyphenyl, 4-(tetrahydro-3-furyloxy)phenyl, 4-ethylthio, 3-ethoxyphenyl, 4-allyloxyphenyl, 4-methoxymethylthiophenyl, 4-(2,2-dichlorovinyloxy)phenyl and 4-(1,1,1-trifluoroethoxy)phenyl.

$R^2$ and $R^3$ preferably represent a $(C_1$–$C_3)$alkyl radical such as methyl, ethyl, i-propyl, or n-propyl, or $R^2$ and $R^3$ together form an alkylene chain which—together with the silicon atom—produces a four- to six-membered ring such as, for example, silacylobutane, silacyclopentane or silacyclohexane.

$R^4$ preferably represents hydrogen, cyano or $(C_1$–$C_4)$alkyl, but particularly preferably for hydrogen.

$R^5$ in a substituted phenyl, preferably represents a phenyl radical of the general formula (C),

 (C)

in which $R^{10}$ and $R^{11}$—independently of one another—may denote H, halogen, $(C_1$–$C_4)$alkyl, $(C_1$–$C_4)$alkoxy, $(C_1$–$C_4)$haloalkyl, phenyl, N-pyrrolyl or a group of the general formula (D)

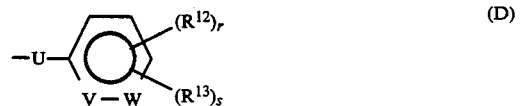 (D)

in which $R^{12}$ and $R^{13}$—independently of one another—may again denote H, halogen, $(C_1$–$C_4)$alkyl, $(C_1$–$C_4)$alkoxy or $(C_1$–$C_4)$haloalkyl.

U represents —$CH_2$—,

—O— or —S—, but preferably —O—;

V and W represent CH or N, where both may simultaneously denote CH; however, where V represents N, W represents CH, and vice versa.

Furthermore, the following is valid regarding formulae (C) 20 and (D):

p, q denote an integer from 0 to 5, with the condition that the sum p+q must denote a number from 1 to 5, r, s denote 0, 1 or 2, with the condition that the sum of r+s must be 0, 1 or 2, and with the condition that, if $R^{10}$ or $R^{11}$ corresponds to the group (D), p and q must denote 0 or 1 and p+q must denote 1 or 2.

Of these radicals for R⁵, radicals of the formula (C) in which (R¹⁰)p denotes H or 4-fluoro, and (R¹¹)q is located in the 3-position of the phenyl radical and denotes the radical

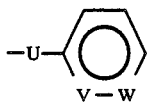

are of particular importance.

R⁵ in optionally substituted pyridyl represents a monosubstituted pyridyl group of the general formula (E),

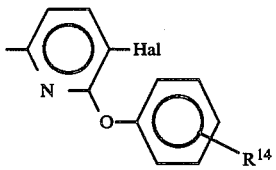

in which
R¹⁴ denotes halogen, apart from I, (C₁-C₄)alkyl, (C₁-C₄)alkoxy or (C₁-C₄)haloalkyl and Hal denotes halogen, particularly fluorine, or H.

R⁵ in optionally substituted thienyl or furyl represents a heterocycle of the general formula (F),

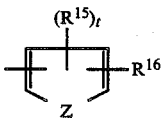

in which
Z denotes O or S,
R¹⁵ denotes H, halogen, (C₁-C₄)alkyl, (C₁-C₄)-alkoxy, (C₁-C₄)haloalkyl, CN or NO₂, and
R¹⁶ denotes optionally substituted benzyl, propargyl or or allyl.

Substituted phenyl radicals for R⁵ are of particular importance for the invention.

The following radicals are specified as typical examples of the group R⁵:

pentafluorophenyl, 5-benzyl-3-furyl, 4-phenoxyphenyl, 3-phenoxyphenyl, 3-(4-fluorophenoxy)phenyl, 3-(4-chlorophenoxy)phenyl, 3-(4-bromophenoxy)phenyl, 3-(3-fluorophenoxy)phenyl, 3-(3-chlorophenoxy)phenyl, 3-(3-bromophenoxy)phenyl, 3-(2-fluorophenoxy)phenyl, 3-(2-chlorophenoxy)phenyl, 3-(2-bromophenoxy)phenyl, 3-(4-methylphenoxy)phenyl, 3-(3-methylphenoxy)-phenyl, 3-(2-methylphenoxy)phenyl, 3-(4 -methoxyphenoxy)phenyl, 3-(3-methoxyphenoxy)-phenyl, 3-(2-methoxyphenoxy)phenyl, 3-(4-ethoxyphenoxy)phenyl, 3-(phenylthio)phenyl, 3-(4-fluorophenylthio)phenyl, 3-(3-fluorophenylthio)phenyl, 3-benzoylphenyl, 3-benzylphenyl, 3-(4-fluorobenzyl)phenyl, 3-(4-chlorobenzyl)phenyl, 3-(3,5-dichlorophenoxy)phenyl, 3-(3,4-dichlorophenoxy)phenyl, 3-(4-chloro-2-methylphenoxy)phenyl, 3-(2-chloro-5-methylphenoxy)phenyl, 3-(4-chloro-5-methylphenoxy)phenyl, 3-(4-ethylphenoxy)phenyl, 3-(3-chloro-5-methoxyphenoxy)-phenyl, 3-(2,5-dichlorophenoxy)phenyl, 3-(3,5-dichlorobenzoyl)phenyl, 3-(3,4-dichlorobenzoyl)phenyl, 3-(4-methylbenzyl)-phenyl, 3-(4-isopropoxyphenoxy)phenyl, 4-fluoro-3-phenoxyphenyl, 4-chloro-3-phenoxyphenyl, 4-bromo-3-phenoxyphenyl, 4-fluoro-3-(4-fluorophenoxy)phenyl, 4-fluoro-3-(4-chlorophenoxy)phenyl, 4-fluoro-3-(4-bromophenoxy)phenyl, 4-fluoro-3-(4-methylphenoxy)phenyl, 4-fluoro-3-(4-methoxyphenoxy)phenyl, 4-fluoro-3-(3-fluorophenoxy)phenyl, 4-fluoro-3-(3-chlorophenoxy)phenyl, 4-fluoro-3-(3-bromophenoxy)phenyl, 4-fluoro-3-(3-methoxyphenoxy)phenyl, 4-fluoro-3-(4-ethoxyphenyl)-phenyl, 4-fluoro-3-(2-fluorophenoxy)phenyl, 3-methoxy-5-phenoxyphenyl, 2-fluoro-3-phenoxyphenyl, 2-fluoro-3-(4-fluorophenoxy)phenyl, 2-fluoro-3-(3-fluorophenoxy)phenyl, 2-fluoro-3-(3-fluorophenoxy)-phenyl, 2-fluoro-3-(2-fluorophenoxy)phenyl, 3-fluoro-5-(4-fluorphenoxy)phenyl, 3-fluoro-5-(fluorophenoxy)-phenyl, 3-fluoro-5-(2-fluorophenoxy)phenyl, 4-methyl-3-phenoxyphenyl, 3-fluoro-5-(4-methylphenoxy)phenyl, 3- fluoro-5-(3-methoxyphenoxy)phenyl, 2-fluoro-5-(4-fluorophenoxyl)phenyl, 2-fluoro-5-(3-fluorophenoxy)phenyl, 2-fluoro-5-(2-fluorophenoxy)phenyl, 2-chloro-3-phenoxyphenyl, 3-fluoro-5-phenoxyphenyl, 2-fluoro-5-phenoxyphenyl, 2-chloro-5-phenoxyphenyl, 2-bromo-5--phenoxyphenyl, 4-chloro-3-(3-methylphenoxy)phenyl, 4-chloro-3-(4-fluorophenoxy)phenyl, 3-chloro-5-phenoxyphenyl, 3-bromo-5-phenoxyphenyl, 4-bromo-3-phenoxyphenyl, 4-trifluoromethyl-3-phenoxyphenyl, 4-fluoro-3-phenylthiophenyl, 4-fluoro-3-benzylphenyl, 3-(2-pyridyloxy)phenyl, 3-(3-pyridyloxy)phenyl, 4-fluoro-3-(2-pyridyloxy)phenyl, 4-chloro-3-(2-pyridyloxy)phenyl, 4-bromo-3-(2-pyridyloxy)phenyl, 4-methyl-3-(2-pyridyloxy)phenyl, 4-fluoro-3-(3-pyridyloxy)phenyl, 4-chloro-3-(3-pyridyloxy)phenyl, 4-bromo-3-(3-pyridyloxy)phenyl, 4-methyl-3-(3-pyridyloxyphenyl), 2-methyl-3-phenylphenyl, 2-methyl-3-(N-pyrrolyl)phenyl, 6-phenoxy-2-pyridyl, 6-(4-fluorophenoxy)-2-pyridyl, 6-(4-chlorophenoxy)-2-pyridyl, 6-(4-bromophenoxy)-2-pyridyl, 6-(4-methylphenoxy)-2-pyridyl, 6-(4-methoxyphenoxy)-2-pyridyl, 6-(4-ethoxyphenoxy)-2-pyridyl, 6-(3-fluorophenoxy)-2-pyridyl, 6-(3-chlorophenoxy)-2-pyridyl, 6-(3-bromophenoxy)-2-pyridyl, 6-(3-methoxyphenoxy)-2-pyridyl, 6-(2-fluorophenoxy)-2-pyridyl, 6-(2 -chlorophenoxy)-2-pyridyl, 6-(2-bromophenoxy)-2-pyridyl, 5-propargyl-3-furyl, N-phthalimidyl, N-3,4,5,6-phthalimidyl, 2-methyl-5-propargyl-3-furyl, 4-t-butylphenyl, 4-methylphenyl, 4-isopropylphenyl, 4-(2-chloro-4-trifluoromethyl-2-pyridyloxy)phenyl, 4-cyclohexylphenyl, 4-difluoromethoxyphenyl, 4-biphenylyl and 4-trimethylsilylphenyl.

Further typical examples of the group

are:
2-allyl-3-methylcyclopent-2-en-1-one-4-yl and 4-phenylindane-2yl.

The present invention also relates to processes for the preparation of the compounds of the general formula (I) wherein
(a) for compounds having X=CH₂, a silane of the general formula (II),

(II)

in which
Y denotes a nucleofugic leaving group such as, for example, halogen or sulfonate, is reacted with an organometallic reagent of the general formula (III),

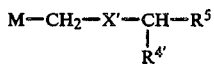 (III)

in which
M corresponds to an alkali metal or alkaline earth metal, particularly Li, Na, K, or Mg,
X' corresponds to a methylene group, and
R$^{4'}$ corresponds to H, CN, F or (C$_1$-C$_4$)alkyl, or
(b) a silane of the general formula (IV) or (V)

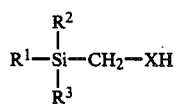 (IV)

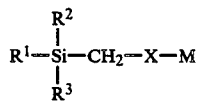 (V)

is reacted with an alkylating agent of the general formula (VI)

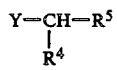 (VI)

if appropriate in the presence of a base, or
(c) a silane of the general formula (VII)

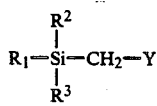 (VII)

is reacted with a XH-acidic compound of the type (VIII)

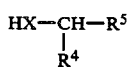 (VIII)

in the presence of a base, or with an organometallic compound of the type (IX)

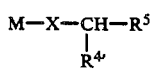 (IX)

or
(d) for compounds where X=CH$_2$, a silane of the general formula (X)

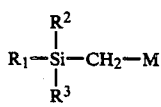 (X)

is reacted with a compound of the type (XI)

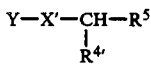 (XI)

or
(e) for compounds where X=CH$_2$, a silane of the general formula (XII)

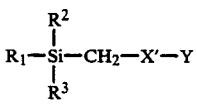 (XII)

is reacted with an organometallic compound of the general formula (XIII)

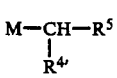 (XIII)

or
(f) a silane of the general formula (XIV)

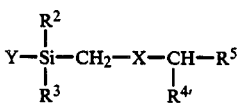 (XIV)

is reacted with an organometallic reagent of the type (XV)

R$^{1'}$-M (XV)

in which
R$^{1'}$ has the meaning of R$^1$ with the exception of nitro, cyano, amino and carbonyl-containing radicals or
(g) a silane of the general formula (XVI)

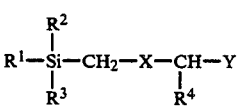 (XVI)

is reacted with an organometallic reagent of the type (XVII)

M-R$^5$ (XVII)

or
(h) for compounds where X=CH$_2$, a silane of the general formula (XXX)

 (XXX)

is reacted with an olefine of the general formula (XXXI)

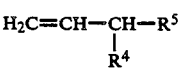 (XXXI)

in the presence of a complex of an element of subgroup VIII of the periodic system as catalyst or (i) for compounds where X=CH$_2$, a silane of the general formula (XXXII)

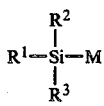 (XXXII)

is reacted with an alkylating agent of the general formula (XXXIII)

Y—CH$_2$—X—CH—R$^5$. (XXXIII)
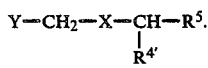

Some of the silanes of the formula (II) to be used as starting compounds in the preparation process (a) are novel and can be prepared, by a process which is known per se from the literature, by starting from a silane of the general formula (XVIII), (XIX) or (XX) and introducing the organic radicals which are still absent using suitable organometallic reagents (see Methoden der org. Chemie [Methods of Organic Chemistry] (Houben-Weyl), Vol. XIII/5, Georg Thieme Verlag, Stuttgart, 1980),

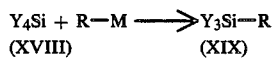

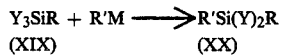

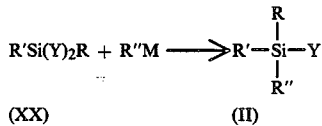

in which

R, R' and R" correspond to the radicals R$^1$, R$^2$ and R$^3$, and Y and M are as defined above.

Some of the organometallic reagents of the general formula (III) to be used as starting compounds in the preparation process (a) are novel and can be prepared, by processes which are known per se from the literature, by initially converting a carbonyl compound of the general formula (XXI),

 (XXI)

in which

R$^4$ and R$^5$ are as defined above, according to Reformatsky (see Methoden der org. Chemie [Methods of Organic Chemistry] (Houben-Weyl), Vol. XIII/2a, Georg Thieme Verlag, Stuttgart 1973), according to Wittig (see Methoden der org. Chemie [Methods of Organic Chemistry] (Houben-Weyl), Vol. E1, Georg Thieme Verlag, Stuttgart 1982) or according to Horner (see L. Horner, Fortschr. Chem. Forsch. 7/1, 1 (1966/67)) to the corresponding α,β-unsaturated ester (XXII),

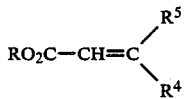 (XXII)

in reducing this by standard methods (see Methoden der org. Chemie [Methods of Organic Chemistry] (Houben-Weyl), Vol. 4/1c and 4/1d, Georg Thieme Verlag, Stuttgart 1980 and 1981) to the alcohol (XXIII),

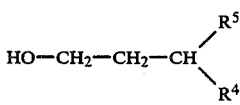 (XXIII)

and then converting this by standard methods (see Methoden der org. Chemie [Methods of Organic Chemistry] (Houben-Weyl), Vol. 5/3 and 5/4, Georg Thieme Verlag, Stuttgart, 1960 and 1962) to a suitable halide (XXIV),

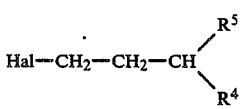 (XXIV)

which finally reacts with an alkali metal or alkaline earth metal to give the required organometallic reagents of the type (III).

Some of the silanes of the general formula (IV) and (V) to be used as starting compounds in the preparation process (b) are novel and can be prepared, by methods which are known per se from the literature (see Methoden der org. Chemie [Methods of Organic Chemistry] (Houben-Weyl), Vol. XIII/5, Georg Thieme Verlag, Stuttgart 1980), by (1) reacting a silane of the general formula (XXV),

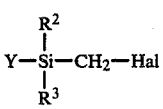 (XXV)

in which

R$^2$, R$^3$ and Y are as defined above and

Hal can be Br or Cl, with an organometallic reagent of the general formula (XV),

R$^{1'}$-M (XV)

then converting the intermediate of the type (VII)

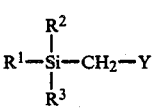 (VII)

Y = Hal by standard methods (see Methoden der org. Chemie [Methods of Organic Chemistry] (Houben-Weyl), Vol. 13/3a, Georg Thieme Verlag, Stuttgart, 1982) to the borane (XXVI),

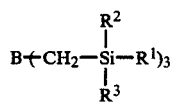 (XXVI)

and finally cleaving this, by methods which are known from the literature (see Methoden der org. Chemie [Methods of Organic Chemistry] (Houben-Weyl), Vol. 13/3C, Georg Thieme Verlag, Stuttgart 1984), to form the desired compounds (IV) (X=O or S).

(2) converting a silane of the general formula (XXVII),

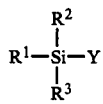 (XXVII)

in which
Y denotes halogen or

, by methods which are known from the literature (see Methoden der org. Chemie [Methods of Organic Chemistry] (Houben-Weyl), Vol. XIII/5, Georg Thieme Verlag, Stuttgart, 1980) to the corresponding metallated silane using an alkali metal, and then reacting with formaldehyde, compounds of the type (IV) having X=O being obtained.

(3) reacting a silane of the general formula (XXVIII),

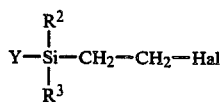 (XXVIII)

in which
$R^2$, $R^3$ and Y are as defined above and
Hal denotes Cl or Br, with an organometallic reagent of the formula (XV)

$R^{1'}$-M (XV)

and reacting the intermediate (XXIX) produced

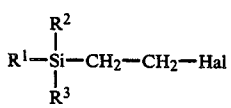 (XXIX)

with an alkali metal or alkaline earth metal, compounds of the tye (V) having X=CH$_2$ being obtained.

The silanes of the general formula (VII)

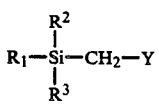 (VII)

to be used as starting compounds in the preparation process (c) can be produced—for Y=Hal—as described above by reaction of the silanes (XXV) with organometallic reagents (XV).

The compounds (VII) having Y=sulfonate can expediently be synthesized by esterification of the alcohols of the type (IV),

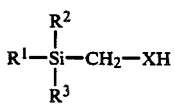 (IV)

with X = O having sulfonic acid radicals, by conventional methods (see Methoden der org. Chemie [Methods of Organic Chemistry] (Houben-Weyl), Vol. IX, Georg Thieme Verlag, Stuttgart, 1955).

Some of the silanes of the general formula (XXX) to be used as starting compounds in the preparation process (h) are novel and can be prepared by methods which are known per se from the literature (see Methoden der org. Chemie [Methods of Organic Chemistry] (Houben-Weyl), Vol. XIII/5, Georg Thieme Verlag, Stuttgart, 1980), by (1) Reacting a silane of the general formula (XXXIV)

 (XXXIV)

with an organometallic reagent of the formula (XI)

$R^{1'}$-M (XI)

or (2) Reducing a silane of the general formula II

 (II)

using metal hydrides such as, for example, sodium hydride or lithium aluminum hydride.

The olefines of the general formula (XXXI)

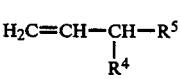 (XXXI)

to be used as starting compounds in the preparation process (h) can be prepared by methods which are known per se from the literature, by reacting an olefine of the general formula (XXXVa) or (XXXVb)

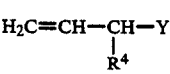 (XXXVa)

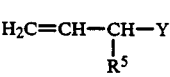 (XXXVb)

with an organometallic reagent, of the general formula (XXXVIa) or (XXXVIb)

M-R⁵ (XXXVIa)

M-R⁴' (XXXVIb)

which can be obtained from the corresponding halogen compound.

Some of the compounds of the formula (XXXI) are novel. The present invention therefore also relates to compounds of the formula (XXXI) in which R⁴ denotes H and
R⁵ denotes a radical of the formula

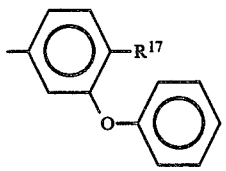

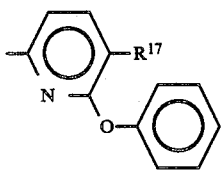  or

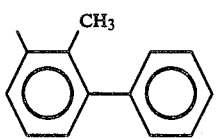

R¹⁷ represents H or halogen, where halogen particularly denotes fluorine.

Some of the metallated silanes of the general formula (XXXII)

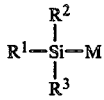 (XXXII)

to be used as starting compounds in the preparation process (i) are novel and can be prepared, by methods which are known from the literature, from the educts (XXVII)

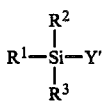 (XXVII)

in which
Y' denotes Hal or

by reaction with an alkali metal.
Some of the alkylating agents (XXXIII)

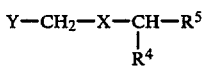 (XXXIII)

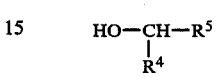

to be used as starting compounds in the preparation process (i) are also novel and can be prepared by methods which are known from the literature (see, for example, Methoden der org. Chemie [Methods of Organic Chemistry] (Houben-Weyl), Vol. V/3, Georg Thieme Verlag, Stuttgart, 1962), for example, for X=O, by reacting an alcohol of the general formula (XXXVII)

$$HO-CH-R^5 \atop R^4 \qquad (XXXVII)$$

with a halogenating agent such as, for example, hydrochloric acid, hydrobromic acid or thionyl chloride, in the presence of paraformaldehyde.

Some of the further compounds of the general formulae (VI), (VIII), (IX), (X), (XI), (XII), (XIII), (XIV), (XV), (XVI) and (XVII) to be used as starting compounds are also novel. They are synthesized by the synthesis stages cited in the text above (see the literature cited above).

The process versions (a), (d), (e), (f), (g) and (i) mentioned are preferably carried out in a diluent whose nature depends on the type of the organometallic compound employed. Suitable diluents are, in particular, aliphatic and aromatic hydrocarbons such as, for example, pentane, hexane, heptane, cyclohexane, petroleum ether, benzine, ligroine, benzene, toluene and xylene, ethers such as, for example, diethyl and dibutyl ether, glycol dimethyl ether, diglycol dimethyl ether, tetrahydrofurane and dioxane, and finally all possible mixtures of the abovementioned solvents.

The reaction temperature in the abovementioned process versions is between −75° C. and +150° C., preferably between −75° C. and +105° C. The starting materials are usually employed in equimolar amounts. However, an excess of one or other of the reaction components is possible.

The same is essentially valid for the abovementioned process versions (b) and (c) as for versions (a) and (d)–(g). When educts of the type (IV) and (VIII) are used, however, further diluents can be employed. Thus, in these cases, ketones such as acetone, methylethyl ketone, methylisopropyl ketone and methyl isobutyl ketone, esters such as methyl and ethyl acetate, nitriles such as, for example, acetonitrile and propionitrile, amides such as, for example, dimethylformamide, dimethylacetamide and N-methylpyrrolidone, and dimethyl sulfoxide, tetramethylene sulfone and hexamethylphosphoric triamide are also suitable as diluents. Inorganic bases such as, for example, alkali metal or alkaline earth metal hydroxides, hydrides, carbonates or bicarbonates, but also organic bases such as, for example, pyridine, triethylamine, N,N-diisopropylethylamine or diazabicyclooctane are used as bases.

The process version (h) mentioned is preferably carried out—in contrast to all other processes for the synthesis of compounds of the general formula I—without diluent. However, solvents such as cyclohexane, petroleum ether, benzene, toluene, tylol and others are also suitable as reaction medium. Complex compounds of the elements of subgroup VIII of the periodic system, such as, for example, $H_2PtCl_6$, $Co_2(CO)_8$, $Rh_4(CO)_{12}$, $Ir_4(CO)_{12}$, or $RhCl[P(C_6H_5)_3]_3$ are used as catalysts (see Methoden der org. Chemie [Methods of Organic Chemistry] (Houben-Weyl), Vol. XIII/5, Georg Thieme Verlag, Stuttgart, 1980, p. 51 et. seq. and the literature cited therein). The catalyst to reacted educts ratio depends on the type of the catalyst and, in the case of $H_2PtCl_6$, for example, varies in the range $1:10^7$ to $1:10^6$.

The compounds of the formula (I) are isolated and, if appropriate, purified by generally conventional methods, for example by evaporation of the solvent (if appropriate under reduced pressure) and subsequent distillation or chromatography, or by distribution of the crude product between two phases and subsequent conventional work-up.

The compounds of the general formula (I) are easily soluble in most organic solvents.

The active compounds are suitable for combating animal pests, in particular insects, arachnida and nematodes, encountered in agriculture, in forestry, in the protection of stored products and of materials, and in the field hygiene, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides,* Melanoplus differentialis and *Schistocerca gregaria.* From the order of the Dermaptera, for example, *Forficula auricularia.* From the order of Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomo, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusiani, *Caporcapsa pomonella,* Pieris spp., Chilo spp., *Pyrausta nubilalis, Ephestia koehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The compounds furthermore have an excellent action against nematodes which are harmful to plants, for example against those of the genera Meloidogyne, Heterodera, Ditylenchus Aphelenchoides, Radopholus, Globodera, Pratylenchus, Longidorus and Xiphinema.

The invention also relates to agents which contain the compounds of the formula (I) in addition to suitable formulation auxiliaries.

The agents according to the invention contain the active compounds of the formula (I), in general to 1–95% by weight. They can be used in the conventional preparations as wettable powders, emulsifiable concentrates, sprayable solutions, dusting agents or granulates.

Wettable powders are preparations which can be dispersed uniformly in water and which also contain, besides the active compound and a diluent or inert substance, wetting agents, for example polyoxethylated alkylphenols, polyoxethylated fatty alcohols or alkyl or alkylphenol sulfonates, and dispersing agents, for example sodium ligninesulfonate, sodium 2,2'-dinaphthylmethane-6,6'-disulfonate, sodium dibutylnaphthalenesulfonate or sodium oleylmethyltaurate.

Emulsifiable concentrates are prepared by dissolving the active compound in an organic solvent, for example butanol, cyclohexanone, dimethylformamide, xylene or, alternatively, higher boiling aromatics or hydrocarbons, with addition of one or more emulsifiers. Examples of emulsifiers which may be used are: calcium salts of alkylarylsulfonic acid, such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condensation products, alkyl polyethers, sorbitol fatty acid esters, polyoxyethylene sorbitol fatty acid esters or polyoxyethylene sorbitol esters.

Dusting agents are obtained by grinding the active compound with finely divided solid substances, for example talc, natural clays such as kaolin, bentonite, poryphillite or diatomaceous earth. Granules can be prepared either by atomizing the active compound onto absorptive, granulated inert material or by applying the active compound concentrates by means of adhesives, for example polyvinyl alcohol, sodium polyacrylate or, alternatively, mineral oils, onto the surface of carrier materials such as sand, kaolinites or granulated inert material. Suitable active compounds can also be prepared in the conventional fashion for the preparation of fertilizer granulates—if desired as a mixture with fertilizers.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, formamidines, tin compounds and substances produced by microorganisms, inter alia. Preferred co-constituents of the mixture are 1. from the group comprising the phosphates, azinphos-ethyl, azinphos-methyl, 1-(4-chlorophenyl)-4-(0-ethyl, S-propyl)phosphoryloxypyrazole (TIA-230), chlorpyrifos, coumaphos, demeton, demeton-S-methyl, diazinon, dichlorvos, dimethoat, ethoprophos, etrimfos, fenitrothion, fenthion, heptenophos, parathion, parathionmethyl, phosalon, pirmiphos-ethyl, pirimiphos-methyl, profenfos, prothiofos, sulprofos, triazophos, trichlorphon.

2. from the group comprising the carbamates, aldicarb, bendiocarb, BPMC (2-(1-Methylpropyl)phenylmethylcarbamate), mutocarboxim, butoxicarboxim, carbaryl, carbofuran, carbosulfan, cloethocarb, isoprocarb, methomyl, oxamyl, primicarb, promecarb, propoxur, thiodicarb.

3. from the group comprising the carboxylates, allethrin, alphametrin, bioallethrin, bioresmethrin, cycloprothrin, cyfluthrin, cyhalothrin, cypermethrin, deltamethrin, α-cyano-3-phenyl-2-methybenzyl 2,2-dimethyl-3-(2-chloro-2-trifluoromethylvinyl)cyclopropanoate (FMC 54800), fenpropathrin, fenfluthrin, fenvalerat, flucythrinate, flumethrin, fluvalinate, permethrin, resmethrin, tralomethrin.

4. From the group comprising the formamidines, amitraz, chlordimeform

5. From the group comprising the tin compounds, azocyclotin, cyhexatin, fenbutatin-oxid 6. Others α- and β-avermectins, *Bacillus thuringiensis*, bensultap, binapacryl, bisclofentezin, buprofecin, cartap, cyromacin, dococol, endosulfan, ethoproxyfen, fenoxycarb, hexythiazox, 3-[2-(4-Ethoxyphenyl)-2-methylpropoxymethyl]-1,3-diphenyl ether (MTI-500), 5-[4-(4-Ethoxyphenyl)-4-methylpentyl]-2-fluoro-1,3-diphenyl ether (MTI-800), 3-(2-chlorophenyl)-3-hydroxy-2-(2-phenyl-4-thiazolyl)propene nitrile (SN 72129), thiocyclam, nuclear polyhedroses and granuloses of viruses.

The active compound concentration of the use forms prepared from the commercially available formulations can vary within wide ranges. The active compound concentration of the use forms can be between 0.0000001 to 100% by weight of active compound, preferably between 0.00001 and 1% by weight.

The application occurs in a conventional fashion which is matched to the methods of use.

The active compounds according to the invention are also suitable for combating ecto- and endoparasites, preferably ectoparasitic insects, in the veterinary medicine field and in the field of animal husbandry.

The active compounds according to the invention are used in a known fashion, such as by oral administration in the form of, for example, tablets, capsules, drenches or granulates, by dermal administration in the form of, for example, dipping, spraying, pour-on, spot-on and powdering, and by parenteral administration in the form of, for example, injection.

The novel compounds of the formula (I) according to the invention can, accordingly, also be particularly advantageously employed in cattle husbandry (for example beef cattle, sheep, pigs and poultry such as chickens, geese etc.). In a preferred embodiment of the invention, the novel compounds are administered orally to the animals, if appropriate in suitable formulations (cf. above) and if appropriate with the drinking water or feed. Since excretion in the droppings occurs in an effective manner, the development of insects in the dropping of the animals can be prevented very simple in this fashion. The suitable dosages and formulations in each case are particularly dependent on the type and stage of development of the productive livestock and also on the infestation intensity of the insects, and can easily be determined and fixed by the conventional methods. In the case of cattle, the novel compounds may be employed, for example, in dosage amounts of 0.1 to 100 mg/kg of body weight.

The following examples illustrate the invention.

A. Formulation Examples (a) A dusting agent is obtained by mixing 10 parts by weight of active compound and 90 parts by weight of talc as inert substance and comminuting in an impact pulverizer.

(b) A wettable powder which can easily be dispersed in water is obtained by mixing 25 parts by weight of active compound, 65 parts by weight of kaolin-containing quartz as inert substance, 10 parts by weight of potassium ligninsulfonate and 1 part by weight of sodium oleoylmethyltaurate as wetting and dispersing agent, and grinding in a pin disc mill.

(c) A dispersion concentrate which can easily be dispersed in water is produced by mixing 20 parts by weight of active compound with 6 parts by weight of alkylphenol polyglycol ether (®Triton X207), 3 parts by weight of isotridecanol polyglycol ether (8 EO) and 71 parts by weight of paraffinic mineral oil, (boiling range, for example, about 255° to about 377° C.), and ground to a fineness of below 5 microns in an abrasive ball mill.

(d) An emulsifiable concentrate can be produced from 15 parts by weight of active compound, 75 parts by weight of cyclohexanone as solvent and 10 parts by weight of oxethylated nonylphenol (10 EO) as emulsifier.

(e) A granulate can be produced from 2 to 15 parts by weight of active compound and an inert granulate support material such as attapulgite, pumice granulate and/or quartz sand.

B. Chemical Examples

Preparation procedures (a) 12.34 g (50 mmol) of 3-(3-phenoxyphenyl)propyl chloride are reacted with 1.22 g (50 mmol) of magnesium in 30 ml of anhydrous ether to form the corresponding Grignard reagent. 11.5 g (50 mmol) of a mixture comprising dimethyl(4-ethoxyphenyl)silyl chloride (66% by weight) and dimethyl(4-ethoxyphenyl)silyl bromide (34% by weight) in 10 ml of ether are added dropwise, and the mixture is subsequently refluxed for 40 h. After cooling to 10° C., 50 ml of ice-water and 150 ml of ether are added to the reaction mixture, which is stirred vigorously. After separating off the aqueous phase, the organic layer is washed successively with 50 ml of water and 50 ml of semisaturated sodium chloride solution, dried over $CaCl_2$, and concentrated. The residue (19.3 g ≙ 99% of theory) is distilled in a bulb tube. 15.6 g (80% of theory) of dimethyl(4-ethoxyphenyl)-3-(3-phenoxyphenyl)propylsilane which passes over at an oven temperature of 220°–240° C./0.1 mbar are obtained. $n_D^{22.3} = 1.5667$.

(b) A mixture of 4.16 g (20 mmol) of 2,3,4,5,6-pentafluoroallylbenzene and 3.79 g (21 mmol) of dimethyl(4-ethoxyphenyl)silane is treated with a little hexachloroplatinic acid and stirred at room temperature. After about 30 min, a vigorously exothermic reaction commences. After a recooling the reaction mixture, the product is purified by bulb tube distillation. 6.71 g (86%) of dimethyl(4-ethoxyphenyl)-(3,2,3,4,5,6-pentafluorophenyl)propylsilane are obtained as a colorless oil which passes over at an oven temperature of 160°–165° C./0.2 mbar. $n_D^{23} = 1.4988$.

The compounds of the formula (I), were $X = CH_2$, listed below are prepared according to these procedures. The following compounds where $X = 0$, S or $NR^6$ can be prepared, for example, by process (b).

| Comp. No. | R¹ | R² | R³ | X | R⁴ | R⁵ | Physical data |
|---|---|---|---|---|---|---|---|
| 1 | 4-ethoxyphenyl (H₅C₂O-C₆H₄-) | $CH_3$ | $CH_3$ | $CH_2$ | H | 3-(4-methoxyphenoxy)phenyl | $n_D^{25} = 1.5670$ |
| 2 | 4-ethoxyphenyl (H₅C₂O-C₆H₄-) | $CH_3$ | $CH_3$ | O | H | 4-tert-butylphenyl (-C₆H₄-C(CH₃)₃) | |
| 3 | 4-ethylphenyl (H₅C₂-C₆H₄-) | $CH_3$ | $CH_3$ | $CH_2$ | H | 3-phenoxyphenyl | $n_D^{22} = 1.5621$ |
| 4 | 2-naphthyl | $CH_3$ | $CH_3$ | $CH_2$ | H | 3-phenoxyphenyl | $n_D^{22} = 1.6042$ |
| 5 | 3,4-difluorophenyl | $CH_3$ | $CH_3$ | $CH_2$ | H | 3-phenoxyphenyl | $n_D^{22} = 1.5480$ |

-continued

| Comp. No. | R¹ | R² | R³ | X | R⁴ | R⁵ | Physical data |
|---|---|---|---|---|---|---|---|
| 6 | 4-H₅C₂O-C₆H₄- | CH₃ | CH₃ | O | H | 3-CH₃-4-(C₆H₄-O)-C₆H₃- | |
| 7 | 4-H₅C₂O-C₆H₄- | C₆H₅ | C₆H₅ | CH₂ | H | 3-(C₆H₅-O)-C₆H₄- | |
| 8 | 4-H₅C₂O-C₆H₄- | CH₃ | CH₃ | O | H | 4-CH₃-C₆H₄- | |
| 9 | C₆H₅-CH₂- | CH₃ | CH₃ | CH₂ | H | 3-(C₆H₅-O)-C₆H₄- | |
| 10 | 3,4-(H₃CO)₂-C₆H₃- | CH₃ | CH₃ | CH₂ | H | 3-(C₆H₅-O)-C₆H₄- | $n_D^{32} = 1.5691$ |

-continued

| Comp. No. | R¹ | R² | R³ | X | R⁴ | R⁵ | Physical data |
|---|---|---|---|---|---|---|---|
| 11 | H₃C—(CH₂)₃— | CH₃ | CH₃ | CH₂ | H | 3-(phenoxy)phenyl | |
| 12 | 4-(ethoxy)phenyl (H₅C₂O-C₆H₄-) | CH₃ | CH₃ | O | H | 3-(4-methoxyphenoxy)phenyl | |
| 13 | 4-(difluoromethoxy)phenyl (F₂CHO-C₆H₄-) | CH₃ | CH₃ | O | H | 2-methylbiphenyl-3-yl | |
| 14 | phenyl | CH₃ | CH₃ | O | H | 3-(phenoxy)phenyl | |
| 15 | 4-chlorophenyl | CH₃ | CH₃ | CH₂ | H | 3-(3-trifluoromethylphenoxy)phenyl | |

-continued

| Comp. No. | R¹ | R² | R³ | X | R⁴ | R⁵ | Physical data |
|---|---|---|---|---|---|---|---|
| 16 | 4-Cl-C₆H₄ | CH₃ | CH₃ | O | H | 2-methyl-3-phenylbenzyl | |
| 17 | 4-F-C₆H₄ | CH₃ | CH₃ | CH₂ | H | 5-methylfurfuryl | |
| 18 | 4-(CH₃)₂N-C₆H₄ | CH₃ | CH₃ | O | H | 3-phenoxyphenyl | |
| 19 | 4-C₂H₅O-C₆H₄ | CH₃ | CH₃ | O | H | allethronyl | |
| 20 | 4-Cl-C₆H₄ | CH₃ | CH₃ | O | H | 2-methyl-3-phenylbenzyl isomer | |
| 21 | 4-Br-C₆H₄ | CH₃ | CH₃ | CH₂ | H | 4-methylbenzyl | |

-continued
| Comp. No. | R¹ | R² | R³ | X | R⁴ | R⁵ | Physical data |
|---|---|---|---|---|---|---|---|
| 22 |  H₃CO–⌬– | CH₃ | CH₃ | O | H | 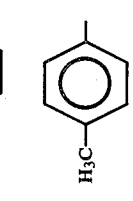 | |
| 23 |  H₅C₂O–⌬– | CH₃ | CH₃ | CH₂ | H |  –CH(CH₃)₂ | $n_D^{26} = 1.5302$ |
| 24 |  H₃C–⌬– | CH₃ | CH₃ | O | H |  | |
| 25 |  Br–⌬– | CH₃ | CH₃ | CH₂ | H | 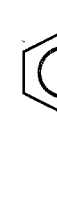 | |
| 26 |  H₅C₂O–⌬– | CH₃ | CH₃ | O | H |  | |
| 27 |  H₅C₂O–⌬– | CH₃ | | CH₂ | H |  | |

-continued

| Comp. No. | R¹ | R² | R³ | X | R⁴ | R⁵ | Physical data |
|---|---|---|---|---|---|---|---|
| 28 | 4-CF₃-C₆H₄ | CH₃ | CH₃ | CH₂ | H | 3-phenoxyphenyl | $n_D^{26} = 1.5302$ |
| 29 | 4-CH₃-C₆H₄ | CH₃ | CH₃ | O | H | 4,5,6,7-tetrahydroisoindole-1,3-dione-2-yl | |
| 30 | 1-naphthyl | CH₃ | CH₃ | CH₂ | H | 3-phenoxyphenyl | |
| 31 | 4-phenoxyphenyl | CH₃ | CH₃ | CH₂ | H | 3-phenoxyphenyl | $n_D^{24} = 1.5848$ |
| 32 | 4-F-C₆H₄ | CH₃ | CH₃ | CH₂ | H | 4,5,6,7-tetrahydroisoindole-1,3-dione-2-yl | |

-continued

| Comp. No. | R¹ | R² | R³ | X | R⁴ | R⁵ | Physical data |
|---|---|---|---|---|---|---|---|
| 33 | F₂CHO–⟨⟩– | CH₃ | CH₃ | CH₂ | H | 2-F, 5-CH₃, phenoxyphenyl | $n_D^{26} = 1.5280$ |
| 34 | H₃CO–⟨⟩– | CH₃ | CH₃ | CH₂ | H | 2-CH₃, 3-phenyl-phenyl | $n_D^{25} = 1.5778$ |
| 35 | H₅C₂O–⟨⟩– | CH₃ | CH₃ | CH₂ | H | 4-CH₃-phenyl | $n_D^{26} = 1.5363$ |
| 36 | H₃CO–⟨⟩– | CH₃ | CH₃ | O | H | 2-CH₃, 3-phenyl-phenyl | |
| 37 | H₅C₂O–⟨⟩– | CH₃ | CH₃ | O | H | 4-phenyl-phenyl | |

-continued

| Comp. No. | R¹ | R² | R³ | X | R⁴ | R⁵ | Physical data |
|---|---|---|---|---|---|---|---|
| 38 | (H₃C)₂N–C₆H₄– | CH₃ | CH₃ | CH₂ | H | 3-phenoxyphenyl (with CH₃) | |
| 39 | Cl–C₆H₄– | CH₃ | CH₃ | O | H | 4-methyl-2-(phenylmethyl)furan | |
| 40 | H₅C₂O–C₆H₄– | C₂H₅ | C₂H₅ | CH₂ | H | 3-phenoxyphenyl (with CH₃) | $n_D^{24} = 1.5626$ |
| 41 | H₅C₂O–C₆H₄– | CH₃ | CH₃ | O | H | 4-methyl-2-(phenylmethyl)furan | |
| 42 | H₅C₂O–C₆H₄– | CH₃ | phenyl | CH₂ | H | 3-phenoxyphenyl | $n_D^{23} = 1.5839$ |

-continued

| Comp. No. | R¹ | R² | R³ | X | R⁴ | R⁵ | Physical data |
|---|---|---|---|---|---|---|---|
| 43 | H₅C₂O—⌬— | CH₂(CH₂)₇CH₂— | CH₂(CH₂)₇CH₂— | CH₂ | H | ⌬—O—⌬(CH₃) | $n_D^{24} = 1.5749$ |
| 44 | F₃C—⌬— | CH₃ | CH₃ | O | H | ⌬—O—⌬(CH₃) | |
| 45 | H₃CO—⌬— | CH₃ | CH₃ | O | H | ⌬—O—⌬(N)(CH₃) | |
| 46 | F₂CHO—⌬— | CH₃ | CH₃ | CH₂ | H | ⌬—⌬(CH₃)(CH₃) | |
| 47 | H₅C₂O—⌬— | CH₂(CH₂)₇CH₂— | CH₂(CH₂)₇CH₂— | CH₂ | H | ⌬—O—⌬(CH₃) | |

-continued

| Comp. No. | R¹ | R² | R³ | X | R⁴ | R⁵ | Physical data |
|---|---|---|---|---|---|---|---|
| 48 | 4-H₅C₂O-C₆H₄- | CH₃ | CH₃ | CH₂ | H | 4-OCHF₂-C₆H₄- | |
| 49 | 4-H₃C-S-C₆H₄- | CH₃ | CH₃ | O | H | 3-phenoxyphenyl | |
| 50 | 5-methylindanyl | CH₃ | CH₃ | CH₂ | H | 3-phenoxyphenyl | |
| 51 | 4-H₃CO-C₆H₄- | CH₃ | CH₃ | CH₂ | H | 2-fluoro-3-phenoxyphenyl | $n_D^{26} = 1.5608$ |
| 52 | 3-H₅C₂O-C₆H₄- | CH₃ | CH₃ | CH₂ | H | 3-phenoxyphenyl | $n_D^{24.5} = 1.5641$ |

-continued

| Comp. No. | R¹ | R² | R³ | X | R⁴ | R⁵ | Physical data |
|---|---|---|---|---|---|---|---|
| 53 | H₅C₂O–⟨phenyl⟩– | CH₃ | CH₃ | O | H | ⟨phenyl⟩–O–⟨phenyl-Cl⟩ (with CH₃) | |
| 54 | H₃C–⟨phenyl⟩– | CH₃ | CH₃ | CH₂ | H | ⟨phenyl-CH₃⟩–O–⟨phenyl⟩ | $n_D^{20} = 1.5692$ |
| 55 | H₅C₂O–⟨phenyl⟩– | CH₃ | CH₃ | CH₂ | H | ⟨phenyl-F, CH₃⟩–O–⟨phenyl⟩ | $n_D^{21} = 1.5550$ |
| 56 | O₂N–⟨phenyl⟩– | CH₃ | CH₃ | CH₂ | H | ⟨phenyl-CH₃⟩–O–⟨phenyl⟩ | |
| 57 | H₅C₂O–⟨phenyl⟩– | CH₃ | CH₃ | S | H | ⟨phenyl-CH₃⟩–O–⟨phenyl⟩ | |

| Comp. No. | $R^1$ | $R^2$ | $R^3$ | X | $R^4$ | $R^5$ | Physical data |
|---|---|---|---|---|---|---|---|
| 58 | 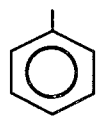 | $CH_3$ | $CH_3$ | $CH_2$ | H | 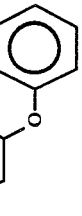 | $n_D^{25}$ = 1.5699 |
| 59 |  | $CH_3$ | $CH_3$ | $NCH_3$ | H | 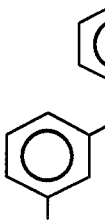 | $n_D^{25}$ = 1.5667 |
| 60 |  | $CH_3$ | $-CH=CH_2$ | $CH_2$ | H | 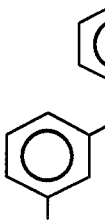 | $n_D^{25}$ = 1.5659 |
| 61 |  | $CH_3$ | $n-C_3H_7$ | $CH_2$ | H | 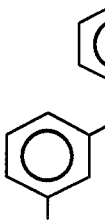 | $n_D^{24}$ = 1.5603 |
| 62 |  | $CH_3$ | $CH_3$ | $CH_2$ | H | 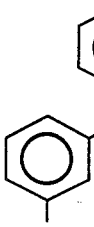 | $n_D^{25}$ = 1.5891 |

-continued

| Comp. No. | R¹ | R² | R³ | X | R⁴ | R⁵ | Physical data |
|---|---|---|---|---|---|---|---|
| 63 | 4-Cl-C₆H₄ | CH₃ | CH₃ | CH₂ | H | cyclohexene-1,2-dicarboximide | $n_D^{24} = 1.5492$ |
| 64 | 4-H₅C₂O-C₆H₄ | —CH₂—CH₂—CH₂— | | CH₂ | H | 3-phenoxyphenyl | $n_D^{24} = 1.5796$ |
| 65 | 3,4-Cl₂-C₆H₃ | CH₃ | CH₃ | CH₂ | H | 3-phenoxyphenyl | $n_D^{23} = 1.5614$ |
| 66 | 4-H₅C₂O-C₆H₄ | CH₃ | C₂H₃ | CH₂ | H | 3-phenoxyphenyl | $n_D^{22.3} = 1.5667$ |
| 67 | 4-H₅C₂O-C₆H₄ | CH₃ | CH₃ | O | H | cyclohexene-1,2-dicarboximide | |

-continued
| Comp. No. | R¹ | R² | R³ | X | R⁴ | R⁵ | Physical data |
|---|---|---|---|---|---|---|---|
| 68 |  H₅C₂O— | CH₃ | CH₃ | CH₂ | H | 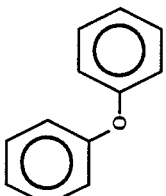 | |
| 69 | 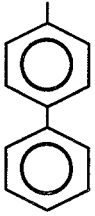 (biphenyl) | CH₃ | CH₃ | CH₂ | H | 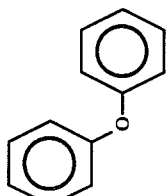 | $n_D^{26} = 1.5669$ |
| 70 | 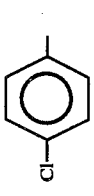 Cl— | CH₃ | CH₃ | CH₂ | H | 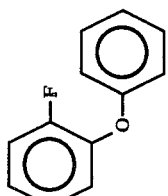 | |
| 71 |  H₅C₂O₂C— | CH₃ | CH₃ | CH₂ | H | 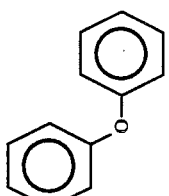 | |
| 72 | 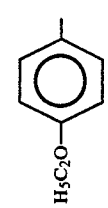 H₅C₂O— | CH₃ | CH₃ | CH₂ | H | 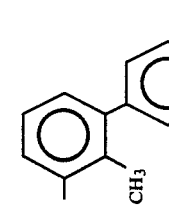 | $n_D^{25} = 1.5691$ |

-continued

| Comp. No. | R¹ | R² | R³ | X | R⁴ | R⁵ | Physical data |
|---|---|---|---|---|---|---|---|
| 73 | 4-Cl-C₆H₄- | CH₃ | CH₃ | O | | H₃C-C(=CH-CH=CH₂)-C(CH₃)=C(-C(=O)-CH₂-) | |
| 74 | 4-Cl-C₆H₄- | CH₃ | CH₃ | O | H | cyclohexene-1,2-dicarboximido (N-linked) | $n_D^{22} = 1.5940$ |
| 75 | 4-H₃CS-C₆H₄- | CH₃ | CH₃ | CH₂ | H | 3-phenoxyphenyl | |
| 76 | 4-H₃C₂O-C₆H₄- | CH₃ | CH₃ | O | H | 2-methylbiphenyl-3-yl | |
| 77 | 4-H₃CO-C₆H₄- | CH₃ | CH₃ | CH₂ | H | (4-methyl-5-phenyl-furan-2-yl)methyl | |

-continued

| Comp. No. | R¹ | R² | R³ | X | R⁴ | R⁵ | Physical data $n_D^{26} = 1.5838$ |
|---|---|---|---|---|---|---|---|
| 78 | 4-Cl-C₆H₄- | CH₃ | CH₃ | CH₂ | H | 2-methyl-3-phenyl-phenyl (biphenyl with CH₃) | $n_D^{26} = 1.5838$ |
| 79 | (H₃C)₂CH- | CH₃ | CH₃ | CH₂ | H | 3-methylphenoxyphenyl | |
| 80 | 4-cyclohexyl-phenyl | CH₃ | CH₃ | CH₂ | H | 3-methylphenoxyphenyl | |
| 81 | 4-H₅C₂O-C₆H₄- | CH₃ | CH₃ | O | H | 2,3-dimethyl-biphenyl | |
| 82 | 4-Cl-C₆H₄- | CH₃ | CH₃ | O | H | 3-methyl-3'-CF₃-phenoxyphenyl | |

-continued
| Comp. No. | R¹ | R² | R³ | X | R⁴ | R⁵ | Physical data |
|---|---|---|---|---|---|---|---|
| 83 |  | CH₃ | CH₃ | O | H |  | |
| 84 |  | CH₃ | CH₃ | CH₂ | H |  | |
| 85 |  | CH₃ | CH₃ | CH₂ | H |  | $n_D^{25} = 1.5462$ |
| 86 |  | CH₃ | CH₃ | CH₂ | H | 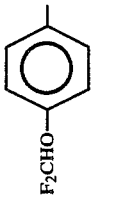 | $n_D^{24} = 1.5650$ |
| 87 | 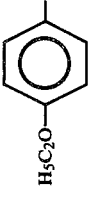 | CH₃ | | O | H |  | |

-continued
| Comp. No. | R¹ | R² | R³ | X | R⁴ | R⁵ | Physical data |
|---|---|---|---|---|---|---|---|
| 88 | HC≡C—CH₂— 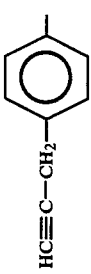 | CH₃ | CH₃ | CH₂ | H | 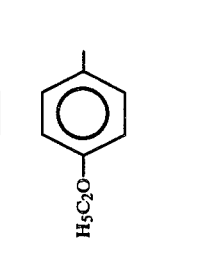 | |
| 89 | H₅C₂O— 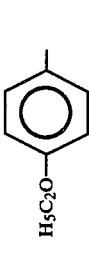 | CH₃ | CH₃ | NCH₃ | H | —C(CH₃)₃ 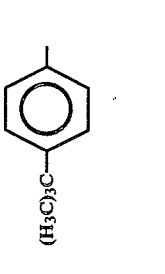 | $n_D^{26} = 1.5620$ |
| 90 | H₅C₂O— 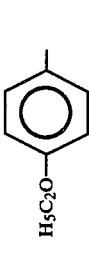 | CH₃ | CH₃ | CH₂ | H |  | $n_D^{24} = 1.5573$ |
| 91 | (H₃C)₃C— 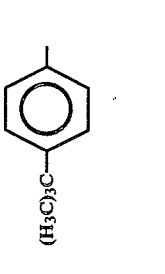 | CH₃ | CH₃ | CH₂ | H | 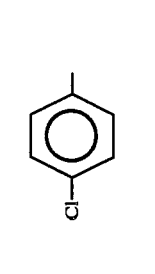 | |
| 92 | Cl— 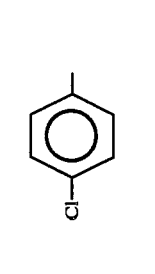 | CH₃ | CH₃ | CH₂ | H | —CH₂ 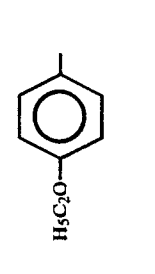 | |
| 93 | H₅C₂O— 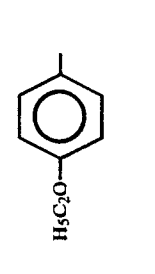 | CH₃ | CH₃ | CH₂ | H |  | $n_D^{23}: 1.4988$ |

-continued

| Comp. No. | R¹ | R² | R³ | X | R⁴ | R⁵ | Physical data |
|---|---|---|---|---|---|---|---|
| 94 | 4-(H₅C₂O)-C₆H₄- | CH₃ | CH₃ | O | H | 4-(CH(CH₃)₂)-C₆H₄- | |
| 95 | 4-((H₅C₂)₂N)-C₆H₄- | CH₃ | CH₃ | CH₂ | H | 3-(C₆H₅O)-C₆H₄- | |
| 96 | 4-(F₃C—CHF—CF₂—O)-C₆H₄- | CH₃ | CH₃ | CH₂ | H | 3-(C₆H₅O)-C₆H₄- | |
| 97 | 4-(H₅C₂O)-C₆H₄- | CH₃ | CH₃ | O | H | 6-(C₆H₅O)-pyridin-2-yl | |
| 98 | 4-(H₅C₂O)-C₆H₄- | CH₃ | CH₃ | O | H | C₆F₅- | |

-continued

| Comp. No. | R¹ | R² | R³ | X | R⁴ | R⁵ | Physical data |
|---|---|---|---|---|---|---|---|
| 99 | 4-F-phenyl | CH₃ | CH₃ | O | H | 2-methyl-biphenyl-3-yl | |
| 100 | 4-F-phenyl | CH₃ | CH₃ | CH₂ | H | 3-phenoxy-4-methylphenyl | $n_D^{19} = 1.5623$ |
| 101 | 4-Br-phenyl | CH₃ | CH₃ | CH₂ | H | 4-methyl-2-phenyl-furan-5-yl-CH₂ | |
| 102 | 4-H₃CO-phenyl | CH₃ | CH₃ | CH₂ | H | 4,5,6,7-tetrahydroisoindole-1,3-dione-2-yl | |
| 103 | 4-H₅C₂O-phenyl | CH₃ | CH₃ | CH₂ | H | 4,5,6,7-tetrahydroisoindole-1,3-dione-2-yl | $n_D^{24} = 1.5388$ |

-continued

| Comp. No. | R¹ | R² | R³ | X | R⁴ | R⁵ | Physical data |
|---|---|---|---|---|---|---|---|
| 104 | 4-Cl-C₆H₄ | CH₃ | CH₃ | CH₂ | H | 6-methyl-2-phenoxypyridin-3-yl | $n_D^{26} = 1.5731$ |
| 105 | 4-C₂H₅O-C₆H₄ | CH₃ | CH₃ | NC₂H₃ | H | 3-phenoxyphenyl | $n_D^{25} = 1.5595$ |
| 106 | 4-Cl-C₆H₄ | CH₃ | CH₃ | O | H | 6-methyl-2-phenoxypyridin-3-yl | |
| 107 | 4-C₂H₅O-C₆H₄ | CH₃ | CH₃ | CH₂ | H | 4-biphenylyl | |
| 108 | 4-H₃CO-C₆H₄ | CH₃ | CH₃ | CH₂ | H | 6-methyl-2-phenoxypyridin-3-yl | |

-continued

| Comp. No. | R¹ | R² | R³ | X | R⁴ | R⁵ | Physical data |
|---|---|---|---|---|---|---|---|
| 109 | 4-HO-C₆H₄ | CH₃ | CH₃ | CH₂ | H | 3-phenoxy-4-methylphenyl | $n_D^{22}$ = 1.5751 |
| 110 | H₃C₂— | CH₃ | CH₃ | CH₂ | H | 3-phenoxy-4-methylphenyl | |
| 111 | 4-H₅C₂O-C₆H₄ | CH₃ | CH₃ | CH₂ | H | 5-(phenoxymethyl)furan-3-yl | |
| 112 | 4-Cl-C₆H₄ | CH₃ | CH₃ | CH₂ | H | 3-phenoxy-4-methylphenyl | $n_D^{22}$ = 1.5778 |
| 113 | cyclohexyl | CH₃ | CH₃ | CH₂ | H | 3-phenoxy-4-methylphenyl | |

-continued

| Comp. No. | R¹ | R² | R³ | X | R⁴ | R⁵ | Physical data |
|---|---|---|---|---|---|---|---|
| 114 | 4-Br-C₆H₄- | CH₃ | CH₃ | CH₂ | H | 3-phenoxyphenyl (with methyl) | $n_D^{20} = 1.5879$ |
| 115 | H₃C-(CH₂)₇- | CH₃ | CH₂ | H | — | 3-phenoxyphenyl (with methyl) | |
| 116 | 4-(CH(OH)CH₃)-C₆H₄- | CH₃ | CH₃ | CH₂ | H | 3-phenoxyphenyl (with methyl) | $n_D^{22} = 1.5740$ |
| 117 | 4-(OC₂H₅)-C₆H₄- | CH₃ | CH₃ | S | H | 4-C(CH₃)₃-C₆H₄- | |
| 118 | (H₃C)₃C-CH₂-CH₂-CH₂- | CH₃ | CH₃ | CH₂ | H | 3-phenoxyphenyl (with methyl) | |

-continued

| Comp. No. | R¹ | R² | R³ | X | R⁴ | R⁵ | Physical data |
|---|---|---|---|---|---|---|---|
| 119 | 4-Cl-C₆H₄- | CH₃ | CH₃ | O | CH₃ | 3-phenoxyphenyl | |
| 120 | 4-H₅C₂O-C₆H₄- | CH₃ | CH₃ | O | CH₃ | 3-phenoxyphenyl | $n_D^{32} = 1.5150$ |
| 121 | H₃C(CH₂)₇- | CH₃ | CH₃ | CH₂ | H | 3-phenoxyphenyl | |
| 122 | 4-H₃CO-C₆H₄- | CH₃ | CH₃ | O | H | N-methyl-tetrahydrophthalimide | |
| 123 | 4-CHO-C₆H₄- | CH₃ | CH₃ | CH₂ | H | 3-phenoxyphenyl | $n_D^{23} = 1.5842$ |

-continued

| Comp. No. | R¹ | R² | R³ | X | R⁴ | R⁵ | Physical data |
|---|---|---|---|---|---|---|---|
| 124 | 4-CH₃-C₆H₄ | CH₃ | CH₃ | CH₂ | H | (cyclohexene-1,2-dicarboximide-N-yl) | $n_D^{25} = 1.5401$ |
| 125 | 4-HOOC-C₆H₄ | CH₃ | CH₃ | CH₂ | H | 3-phenoxyphenyl | |
| 126 | 3,4-(CH₃)₂-C₆H₃ | CH₃ | CH₃ | CH₂ | H | 3-phenoxyphenyl | |
| 127 | 4-H₅C₂O-C₆H₄ | CH₃ | CH₃ | O | –C≡CH | 3-phenoxyphenyl | |
| 128 | 4-H₅C₂O-C₆H₄ | CH₃ | CH₃ | CH₂ | CN | 3-phenoxyphenyl | |

-continued
| Comp. No. | $R^1$ | $R^2$ | $R^3$ | X | $R^4$ | $R^5$ | Physical data |
|---|---|---|---|---|---|---|---|
| 129 |  | CH$_3$ | CH$_3$ | CH$_2$ | H |  | |
| 130 | 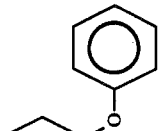 | CH$_3$ | CH$_3$ | CH$_2$ | H |  | |
| 131 | 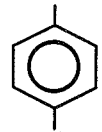 | CH$_3$ | CH$_3$ | CH$_2$ | H | " | |
| 132 |  | CH$_3$ | CH$_3$ | CH$_2$ | F | 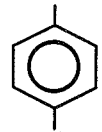 | |
| 133 |  | CH$_3$ | CH$_3$ | CH$_2$ | F | 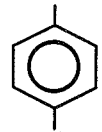 | |

-continued

| Comp. No. | R¹ | R² | R³ | X | R⁴ | R⁵ | Physical data |
|---|---|---|---|---|---|---|---|
| 134 | " | CH₃ | CH₃ | CH₂ | F | 2-fluorophenyl-O-phenyl | |
| 135 | " | CH₃ | CH₃ | CH₂ | F | 3-fluoro-6-methylpyridin-2-yl-O-phenyl | |
| 136 | " | CH₃ | CH₃ | CH₂ | H | 6-methylpyridin-2-yl-O-(4-fluorophenyl) | |
| 137 | " | CH₃ | CH₃ | CH₂ | H | 6-methylpyridin-2-yl-O-(3-CF₃-phenyl) | |
| 138 | " | CH₃ | CH₃ | CH₂ | H | 6-methylpyridin-2-yl-O-(2-fluorophenyl) | |

C. Biological Examples

EXAMPLE 1

Field beans (*Vicia faba*) which were heavily infested with Cowpea aphid (*Aphis craccivora*) were sprayed with aqueous dilutions of emulsion concentrates containing 1000 ppm of active compound until the stage where dripping commenced. After 3 days, the mortality was 100% in each case for the preparations containing the active compounds of Examples 5, 33, 51, 54, 55, 68, 70, 75, 85, 86, 90, 112 and 114.

EXAMPLE 2

Bean plants (*Phaseolus vulgaris*) which were heavily infested with greenhouse whitefly (*Trialeurodes vaporarium*) were sprayed with aqueous dilutions of emulsion concentrates (1000 ppm of active compound) unit dripping commenced. 14 days after the plants were placed in a greenhouse, they were inspected microscopically, with a result of 100% mortality in each case of the preparations containing the active compound of Examples 33, 54, 55, 68, 90 and 104.

EXAMPLE 3

Experimental procedure: analogous to Example 2
Experimental animals: *Tetranychus urticae* (two-spotted spider mite)
Experimental plants: *Phaseolus vulgaris* (kidney bean)
Amount applied: 1000 ppm of active compound in the spray liquid
After 8 days, an activity of 100% mortality was observed for compound 33.

EXAMPLE 4

Bean plants, (*Phaseolus vulgaris*) which were heavily infested with citrus mealybug (*Pseudococcus citri*) were sprayed with aqueous dilutions of emulsion concentrates (1000 ppm of active compound in the spray liquid in each case) until the stage where dripping commenced. After standing for 7 days in a greenhouse at 20°-25° C., the inspection was carried out. 100% mortality was determined for the compounds according to Examples 5, 33, 51, 54, 55, 68, 70, 75, 85, 86, 90, 112 and 114.

EXAMPLE 5

Milkweed bugs (*Oncopeltus fasciatus*) were treated with aqueous dilutions of emulsion concentrates (1000 ppm of active compound in the spray liquid in each case) of the active compounds of Examples 5, 33, 51, 54, 55, 68, 70, 75, 85, 86, 90, 112 and 114. The bugs were subsequently placed at room temperature in containers provided with lids which were permeable to air. 5 days after the treatment, the mortality was determined and was 100% in each individual case.

EXAMPLE 6

The insides of the bases of Petri dishes coated with a synthetic nutrient medium were sprayed, after solidification of the feedstuff paste, in each case with 3 ml of an aqueous emulsion containing 2000 ppm of active compound. After the spray coating had dried and 10 larvae of the common cotton worm (*Prodenia litura*) were inserted, the dishes were stored for 7 days at 21° C. and the degree of action of the respective compound (expressed in % mortality) was determined. The compounds 5, 33, 51, 54, 55, 68, 70, 85, 86, 90, 100, 104, 112 and 114 produced an activity of 100% in each case in this test.

EXAMPLE 7

Bean leaves (*Phaseolus vulgaris*) were treated with an aqueous emulsion of the compound of Example 68 in a concentration of 1000 ppm (based on the active compound) and placed with similarly treated larvae of the Mexican bean beetle (*Epilachna varivestis*) in observation cages. An evaluation of the 48 hours showed 100% destruction of the experimental animals. The compounds according to Examples 33, 51, 55 and 70 proved similarly effective.

EXAMPLE 8

1 ml of Example 68 as active compound in acetone with a concentration of 1000 ppm was applied evenly to the inside of the lid and the base of a Petri dish using a pipette, and the dish was left open until the solvent had evaporated completely. 10 houseflies (*Musca domestica*) were then placed in the Petri dishes, the dishes were closed using the lid, and a 100% destruction of the experimental animals was determined after 3 hours. The compounds according to Examples 5, 33, 51, 55, 70 and 86 also proved effective.

EXAMPLE 9

1 ml of an active compound solution in acetone having a concentration of 2000 ppm was applied evenly to the inside of the lid and the base of a Petri dish using a pipette. After the solvent had evaporated completely, 10 larvae (L4) of the German cockroach (*Blatella germanica*) were inserted into each Petri dish, and the dishes were closed using the lids. After 72 hours, the action (expressed in % mortality) was determined. The compounds 1, 3, 5, 28, 33, 51, 54, 55, 68, 70, 75, 85, 86, 100, 112 and 114 gave an activity of 100% in each case in this test.

We claim:

1. A compound of the formula

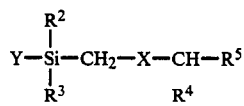

wherein
X is $CH_2$, O or S,
Y is halogen or sulfonate,
$R^2$ and $R^3$, independently of one another, are ($C_1$-$C_3$)alkyl, ($C_2$-$C_8$)alkenyl or phenyl,
$R^4$ is H, CN, $CCl_3$, F or ($C_1$-$C_4$)alkyl,
$R^5$ is a phenyl of the formula

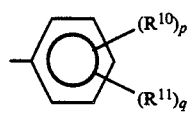

(C)

in which $R^{10}$ and $R^{11}$, independently of one another are H, halogen, ($C_1$-$C_4$)alkyl, ($C_1$-$C_4$)alkoxy, ($C_1$-$C_4$)haloalkyl, phenyl, N-pyrrolyl; or or a group of the formula

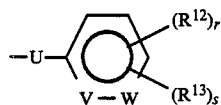  (D)

in which $R^{12}$ and $R^{13}$, independently of one another are H, halogen, $(C_1-C_4)$alkyl, $(C_1-C_4)$alkoxy or $(C_1-C_4)$haloalkyl, U being $CH_2$, CO, O or S, V and W being CH or N, however, when either V or W is N, the other is CH, p and q, independent of one another are integers from 0 to 5, but with the condition that the sum of p+q is an integer from 1 to 5, r and s, independent of one another, are 0, 1 or 2, with the condition that the sum of r+s is 0, 1 or 2 and with the further condition that, if either $R^{10}$ or $R^{11}$ is a group corresponding to formula (D), p and q must be 0 or 1 and p+q must be 1 or 2; or $R^5$ is a pyridyl group of the formula

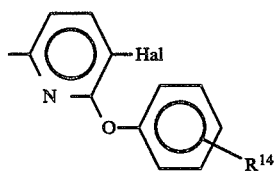  (E)

in which $R^{14}$ is H, halogen other than I, $(C_1-C_4)$alkyl, $(C_1-C_4)$alkoxy or $(C_1-C_4)$haloalkyl, and Hal is halogen or H;

or $R^5$ is a thienyl or furyl of the formula

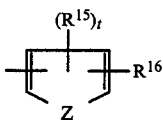  (F)

in which Z is O or S, $R^{15}$ is H, halogen, $(C_1-C_4)$alkyl, $(C_1-C_4)$alkoxy, $(C_1-C_4)$haloalkyl, CN or $NO_2$, and $R^{16}$ is benzyl, propargyl or allyl.

2. The compound of claim 1 in which $R^5$ is the phenyl of the formula

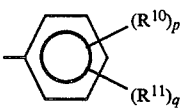  (C)

3. The compound of claim 2 in which $(R^{10})_p$ is H or 4-fluoro, and $(R^{11})_q$ is substituted at the 3-position of the phenyl radical and is the radical

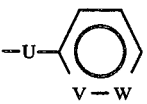

4. The compound of claim 3 in which U is O.

5. The compound claimed in claim 1 wherein $R^{14}$ is fluorine or H.

* * * * *